United States Patent
Harris et al.

(12)

(10) Patent No.: US 6,265,414 B1
(45) Date of Patent: *Jul. 24, 2001

(54) TREATING SLEEP DISORDERS USING DESLORATADINE

(75) Inventors: Alan G. Harris, New York, NY (US); Domenic G. Iezzoni, Ridgewood, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/563,553

(22) Filed: May 3, 2000

Related U.S. Application Data

(63) Continuation of application No. 09/425,715, filed on Oct. 22, 1999, now Pat. No. 6,114,346.

(51) Int. Cl.$^7$ .............................................. A61K 31/4375
(52) U.S. Cl. ............................................................ 514/290
(58) Field of Search .............................................. 514/290

(56) References Cited

U.S. PATENT DOCUMENTS

| | | | |
|---|---|---|---|
| 3,536,809 | 10/1970 | Applezweig | 424/28 |
| 3,598,123 | 8/1971 | Zaffaroni | 128/268 |
| 3,845,770 | 11/1974 | Theeuwes et al. | 128/260 |
| 3,916,899 | 11/1975 | Theeuwes et al. | 128/260 |
| 3,940,485 | 2/1976 | Levinson et al. | 424/250 |
| 4,008,796 | 2/1977 | Aylon | 198/460 |
| 4,282,233 | 8/1981 | Vilani | 424/267 |
| 4,371,516 | 2/1983 | Gregory et al. | 424/22 |
| 4,552,899 | 11/1985 | Sunshine et al. | 514/568 |
| 4,659,716 | 4/1987 | Villani et al. | 514/290 |
| 4,731,447 | 3/1988 | Schumacher et al. | 546/93 |
| 4,777,170 | 10/1988 | Heinrich | 514/226.2 |
| 4,783,465 | 11/1988 | Sunshine et al. | 514/255 |
| 4,804,666 | 2/1989 | Piwinski et al. | 514/278 |
| 4,863,931 | 9/1989 | Schumacher et al. | 514/290 |
| 4,990,535 | 2/1991 | Cho et al. | 514/556 |
| 5,019,591 | 5/1991 | Gardner et al. | 514/461 |
| 5,089,496 | 2/1992 | Piwinski et al. | 514/253 |
| 5,100,675 | 3/1992 | Cho et al. | 424/468 |
| 5,314,697 | 5/1994 | Kwan et al. | 424/480 |
| 5,595,997 | 1/1997 | Abert et al. | 514/290 |
| 5,731,319 | 3/1998 | Aberg et al. | 514/290 |
| 5,900,421 | 5/1999 | Handley et al. | 514/290 |
| 5,939,426 | 8/1999 | McCullough | 514/290 |

FOREIGN PATENT DOCUMENTS

| | | |
|---|---|---|
| 0 288640 A1 | 10/1987 | (EP) . |
| 0 396404 A1 | 5/1990 | (EP) . |
| 0 396404 B1 | 5/1990 | (EP) . |
| WO 85/03707 | 8/1985 | (WO) . |
| WO 92/11034 | 12/1991 | (WO) . |
| WO 92/00293 | 1/1992 | (WO) . |
| WO 92/203774 | 5/1992 | (WO) . |
| WO 96/16641 | 12/1995 | (WO) . |
| WO 96/20708 | 12/1995 | (WO) . |
| WO 98/34614 | 8/1998 | (WO) . |

OTHER PUBLICATIONS

Hartauer, et al., "A comparison of diffuse reflectance FT–IR spectroscopy and DSC in the characterization of a drug–excipient interaction", Drug Development and Industrial Pharmacy, 1991, 17(4):617–630.

Blaug, et al., "Interaction of dextroamphetamine sulfate with stpay–dried lactose", J. of Pharm. Sciences, 1972, 61(11):1770–1775.

Castello, et al., "Discoloration of tablets containing amines and lactose", J. of Pharm. Sciences, 1962, 51(2):106–108.

Wade, et al., *Handbook of Pharmaceutical Excipients* ($2^{nd}$ *edition*), American Pharma. Assoc. & the Pharma. Press, Royal Pharma. Society of G. Britain, pp. 257–259 (1994).

Wirth, et al., "Maillard reaction of lactose and fluoxetine hydrochloride, a secondary amine", J. of Pharm. Sciences, 1998, 87(1):31–39.

Babe, et al., The Pharmacological Basis of Therapeutics ($9^{th}$ edition), The McGraw–Hill Co. Inc., pp. 581–599 (1996).

Andersen, et al., "Adverse drug interactions clinically important for the dermatologist", Arch Dermatol, 1995, 131:468–473.

Barnett, et al., *New Perspectives in Histamine Research*, Birkhauser Verlag Basel, pp. 181–196 (1991).

Berge, et al., "Pharmaceutical slats", J. of Pharm. Sciences, 1977, 66(1):1–19..

Berthon, et al., "In Vitro inhibition, by loratadine and descarboxyethoxyloratadine, of histamine release from human basophils, and of histamine release and intracellular calcium fluxes in rat basophilic leukemia cells (RBL–2H3)", Biochem. Pharm., 1994 47(5):789–794.

Brandes, et al., "Enhanced cancer growth in mice administered daily human–equivalent doses of some H1–antihistamines: predictive in vitro correlates", J. of the National Cancer Inst., 1994, 86(10):770–775.

Brandes, et al., "Stimulation of malignant growth in rodents by antidepressant drugs at clinically relevant doses", Cancer Research, 1992, 52:3796–3800.

Brion, et al., "Evaluation of the antimuscarinic activity of atropine, terfenadine and mequitazine in healthy volunteers", Br. J. clin. Pharmac. 1988, 25:27–32.

Carmeliet, "Voltage– and time–dependent block of the delayed K+ current in cardiac myocytes by dofetilide", The J. of Pharm. And Experimental Therapeutics, 1992, 262(2):809–817.

(List continued on next page.)

*Primary Examiner*—Phyllis G. Spivack
(74) *Attorney, Agent, or Firm*—Thomas D. Hoffman

(57) ABSTRACT

Methods of treating and/or preventing sleep disorders in a human afflicted with upper airway passage allergic inflammation and/or congestion associated with allergic rhinitis, including seasonal allergic rhinitis or perennial allergic rhinitis, by administering a therapeutically effective amount of desloratadine, alone or in combination with other active such as a decongestant, e.g., pseudoephedrine are disclosed.

23 Claims, No Drawings

OTHER PUBLICATIONS

Cheung, et al., "Investigation of anti–motion sickness drugs in the squirrel monkey", J. Clin. Pharmacol, 1992, 32:163–175.

Clissold, et al., "Loratadine a preliminary review of its pharmacodynamic properties and therapeutic efficacy", Drugs, 1989, 37:42–57.

Cooke, "Glycopyrrolate in bladder dysfunction", SA Medical Journal, 1983, 3.

Craft, "Torsade de pointes after astemizole overdose", Br. Medical Journal, 1986, 292:660.

Dorje, et al., "Antagonist binding profiles of five cloned human muscarinic receptor subtypes", The J. of Pharm. And Experimental Therapeutics, 1991, 256:727–733.

Lunde, Side Effects of Drugs Annual 12; A worldwide yearly survey of new data and trends, Elsevier Science Publishers B.V., 1988, 142–143.

Ebert, "Soft elastic gelatin capsules: a unique dosage form", Pharmaceutical Technology, 1977, 44–50.

Gengo, "Dilemma: Antihistamine selection: Use vs. Side effects", U.S. Pharmacist, Nov. 1990, 59–92.

Regula Herzog, et al., *Annual Review of Gerontology and Geriatrics,* 1989, 9:74–119.

Hilbert, et al., "Pharmacokinetics and dose proportionality of loratadine", J. Clin. Pharmacol. 1987, 27:694–698.

Housley, et al., "Histamine and related substances influence neurotransmission in the semicircular canal", Hearing Research, 1988, 35:87–98.

Jankowski, et al., "Effect of terfenadine on nasal provocation", Int. Arch. Allergy Immunol., 1993, 101:311–317.

Kaliner, "Nonsedating antihistamines: Pharmacology, clinical efficacy and adverse effects", American Family Physician, Mar. 1992, 45(3):1337–1342.

Kleine–Tebbe, et al., "Inhibition of IgE– and non–IgE–mediated histamine release from human basophil leukocytes in vitro by a histamine H1–antagonist, desethoxycarbonyl–loratadine", J. Allergy Clin. Immunol., 1994, 93:494–500.

Knowles, "Astemizole and terfenadine–induced cardiovascular effects", The Canadian J. of Hospital Pharmacy, Feb. 1992, 45(1):33–37.

Kohl, et al., "Lack of effects of astemizole on vestibular ocular reflex, motion sickness, and cognitive performance in man", Aviation, Space, and Environmental Medicine, Dec. 1987, 1171–1174.

Kohl, et al., "New pharmacologic approaches to the prevention of space/motion sickness", J. Clin. Pharmacol., 1991, 31:934–946.

Kohl, et al., "Control of nausea and autonomic dysfunction with terfenadine, a peripherally acting antihistamine", Aviation, Space, and Environmental Medicine, May 1991, 392–396.

Kubo, et al., "Antimuscarinic effects of antihistamines: Quantitative evaluation by receptor–binding assay", Japan J. Pharmacol., 1987, 43:277–282.

Lathers, et al., "Pharmacology in space: Part 2. Contolling motion sickness", TiPS, Jun. 1989, 10:243–250.

Levin, et al., "Direct measurement of the anticholinergic activity of a series of pharmacological compounds on the canine and rabbit urinary bladder", The J. of Urology, Aug. 1982, 128:396–398.

Lunde, *Side Effects of Drugs Annual 14,* Elsevier Science Publishers B.V., 1990, 135–143.

Massad, et al., "The pharmacokinetics of intravesical and oral oxybutynin chloride", The J. of Urology, Aug. 1992, 148:595–597.

Miadonna, et al., "Inhibitory effect of the H1 antagonist loratadine on histamine release from human basophils", Int. Arch Allergy Immunol., 1994, 105:12–17.

Mirakhur, et al., "Glycopyrrolate: pharmacology and clinical use", Anaesthesia, 1983, 38:1195–1204.

Mitchelson, "Pharmacological agents affecting emesis: A review (Part II)", Drugs, 1992, 43(4):443–463.

Muskat, et al., "The use of scopolamine in the treatment of detrusor instability", The J. of Urology, 1996, 156:1989–1990.

Nelemans, *Side Effects of Drugs Annual 12,* Elsevier Science Publishers B.V., 1988, 144–147.

Parkinson, et al., "Evaluation of Loratadine as an inducer of liver microsomal cytochrome P450 in rats and mice", Biochemical Pharmacology, 1992, 43(10):2169–2180.

Peggs, et al., "Antihistamines; The old and the new", American Family Physician, Aug. 1995,52(2):593–600.

Petrin, "Bewegungskrankheit und ihre therapie/Eine Ubersicht (Motion sickness and its treatment)", Schweiz, Rundschau Med., 1974, (PRAXIS) 63:79–81.

Quercia, et al., "Focus on Laratadine: A new second–generation nonsedating H1–receptor antagonist", Hosp. Formul., 1993, 28:137–153.

Resnick, "Urinary incontinence", The Lancet, 1995, 346:94–99.

Roman, et al., "Loratadine–A review of recent finding in pharmacology pharmacokinetics, efficacy, and safety, with a look at its use in combination with pseudoephedrine", Clin. Reviews in Allergy, 1993, 11:89–110.

Simons, "H1–receptor antagonist Comparative tolerability and safety", Drug Safety, 1994, 10(5):350–380.

Temple, et al., "Loratadine, an antihistamine, blocks antigen–and ionophore–induced leukotriene release from human lung in vitro", Prostaglandins, Apr. 1988, 35(4):549–554.

Sunahara, et al., "Pharmacological interventions for motion sickness: Cardiovascular Effects", Aviation, Space and Environmental Medicine, Sep. 1987, A270–A276.

Zhong, et al., "HPLC–Determination of Loratadine and its active metabolite descarboethoxyloratadine in human plasma", Pharmazie, 1994, 49(H. 10):736–739.

Yarker, et al., "Oxybutynin,. A review of its pharmacodynamic and phamocikinetic properties, and its therapeutic use in detrusor instability", Drugs and Aging, 1995, 6(3):243–262.

Wood, et al., "Mechanisms of antimotion sickness drugs", Aviation, Space, and Environmental Medicine, Sep. 1987, A262–A265.

Wood, "Antimotion sickness and antiemetic drugs", Drugs, 1979, 17:471–479.

Wein, "Pharmacology of incontinence", Urologic Clinics of North America, Aug. 1995, 22(3):557–577.

Van Cauwenberge, "New data on the safety of Loratadine", Drug Invest., 1992, 4(4):283–291.

McCue, "Safety of antihistamines in the treatment of allergic rhinitis in elderly patients", Arch. Fam. Med., 1996, 5:464–468.

TREATING SLEEP DISORDERS USING DESLORATADINE

CROSS-REFERERENCE TO RELATED APPLICATION

This application is a continuation application of U.S. Ser. No. 09/425,715, filed Oct. 22, 1999 and now U.S. Pat. No. 6,114,346.

FIELD OF THE INVENTION

The present invention relates to treating and/or preventing sleep disorders in a human afflicted with upper airway passage allergi inflammation and congestion by administering a therapeutically effective amount of desloratadine.

BACKGROUND OF THE INVENTION

Sleep disorders are becoming increasingly prevalent in our fast paced, "doing business around the clock" society. It is estimated that 40 million Americans suffer from various sleep disorders. Further, 25 million more Americans suffer from intermittent-sleep-related disorders. Sleep disorders have various etiologies including stress induced by environmental and life style factors, physical factors, such as disease or obesity, and psychiatric disorders, such as depression. Further, allergic rhinitis can cause sleep disorders. Allergic rhinitis is a common cause of breathing disorders associated with nasal congestion which can lead to disordered sleep. Upper airway passage congestion has been observed in over 80% of patients afflicted with seasonal allergic rhinitis and/or perennial allergic rhinitis. The allergic rhinitis congestion may be associated with post nasal drip, sinusitis, nasal polyps, each of which may worsen the upper airway passage air flow (breathing). See, Young, T. et al, *Journal of Allergy Clin. Immunol.*, pp. S 757–762, February 1997, and Finn, L. et al., *Am. J. Respiratory Critical Care Medicine*, Vol. 157, No. 3, p. A61, March 1998. Sleep disorders encompass snoring, sleep apnea, insomnia, narcolepsy, restless legs syndrome, sleep terrors, sleep walking and sleep eating. Possible treatment can be as simple as behavior modification or it can be as involved as mechanical, surgical, or pharmacologic intervention. For example, sleep apnea can be treated by a mechanical device called a pneumatic splint or by allergen proof pillow casings, nasal steroids or pilocarpine. Narcolepsy can be treated with tricyclic anti-depressants, monoamine oxidase inhibitors or amphetamines. Valium® and other benzadiazepines or melatonin may be used to treat insomnia. Restless legs syndrome can be treated with Valium®.

However, the need for improved non-invasive treatment of sleep disorders in patients suffering from upper airway passage congestion is demonstrated by the proliferation of sleep research centers and sleep clinics purporting to offer relief as well as by the proliferation of ENT services ("sinus clinics") and nasal polyp surgery and upper airway surgery.

SUMMARY OF THE INVENTION

The present invention provides a method of treating and/or preventing sleep disorders in a human afflicted with upper airway passage allergic inflammation and/or congestion comprising administering a therapeutically effective amount of desloratadine.

The present invention also provides a method of treating and/or preventing sleep disorders in a human afflicted with upper airway passage allergic inflammation and/or congestion associated with allergic rhinitis comprising administering a therapeutically effective amount of desloratadine The present invention further provides a method of treating and/or preventing sleep disorders in a human afflicted with upper airway passage allergic inflammation and/or congestion comprising administering a therapeutically effective amount of desloratadine in association with a therapeutically effective amount of an upper airway passage decongestant.

DETAILED DESCRIPTION OF THE INVENTION

The present invention is particularly effective in treating and/or preventing sleep disorders in a patient suffering from upper airway passage allergic inflammation and/or congestion associated with allergic rhinitis and the resultant disordered sleep. The term "allergic rhinitis" as used herein means seasonal allergic rhinitis and perennial allergic rhinitis. The terms "sleep disorders" and "disordered sleep" as used herein mean disordered, interrupted or fragmented sleep characterized by events including, but not limited to, snoring, periods of sleep apnea, insomnia, narcolepsy, restless legs syndrome, sleep terrors, sleep walking, sleep eating and daytime somnolence. The magnitude of a prophylactic or therapeutically effective dose of desloratadine in the acute or chronic management of sleep disorders associated with upper airway passage congestion will vary with the severity of the condition to be treated and the route of administration. The therapeutically effective amount, and perhaps the frequency, will also vary according to the age, body weight, and response of the individual patient. In general, the total daily therapeutically effective amount, for the conditions described herein, is from about 1 mg to about 20 mg administered in single or divided doses orally, topically, transdermally, or locally by inhalation. For example, a preferred oral daily dose range should be from about 5 mg to about 20 mg.

U.S. Pat. No. 4,659,716 discloses desloratadine as a non-sedating antihistamine and methods of making desloratadine, pharmaceutical compositions containing it and methods of using desloratadine compositions to treat allergic reaction in mammals. U.S. Pat. No. 5,595,997 discloses pharmaceutical compositions containing desloratadine and methods of a using desloratadine for treating allergic rhinitis. U.S. Pat. No. 4,659,716 and U.S. Pat. No. 5,595,997 are both incorporated by reference herein.

Desloratadine is available from Schering Corporation, Kenilworth, N.J.

The pharmaceutical compositions of desloratadine can be adapted for any mode of administration, e.g., for oral, parenteral, e.g., subcutaneous ("SC"), intramuscular ("IM"), intravenous ("IV") and intraperitoneal ("IP"), or by topical, vaginal or rectal administration (e.g. suppositories). Preferably desloratadine is administered orally.

Such compositions may be formulated by combining desloratadine or an equivalent amount of a pharmaceutically acceptable salt thereof with a suitable, inert, pharmaceutically acceptable carrier or diluent which may be either solid or liquid. Desloratadine may be converted into the pharmaceutically acceptable acid addition salts by admixing it with an equivalent amount of a pharmaceutically acceptable acid. Typically suitable pharmaceutically acceptable acids include the mineral acids, e.g., $HNO_3$ $H_2SO_4$, $H_3PO_4$, HCl, HBr, organic acids, including, but not limited to, acetic, trifluoroacetic, propionic, lactic, maleic, succinic, tartaric, glucuronic and citric acids as well as alkyl or arylsulfonic acids, such as p-toluenesulfonic acid, 2-naphthalenesulfonic acid, or methanesulfonic acid. The preferred pharmaceutically acceptable salts are trifluoroacetate, tosylate, mesylate, and chloride. Desloratadine is more stable as the free base than as an acid addition salt and the use of the desloratadine free base in pharmaceutical compositions of the present invention is preferred.

Solid form preparations include powders, tablets, dispersible granules, capsules, cachets and suppositories. The powders and tablets may include from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Ed., Mack Publishing Co., Easton, Pa.

Liquid form preparations include solutions, suspensions and emulsions. As an example may be mentioned water or water-propylene glycol solutions for parenteral injection. Solid form preparations may be converted into liquid preparations shortly before use for either oral or administration. Parenteral forms to be injected intravenously, intramuscularly or subcutaneously are usually in the form of sterile solutions and may contain tonicity agents (salts or glucose), and buffers. Opacifiers may be included in oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active component, e.g., an effective amount to achieve the desired purpose.

Additional Active Ingredients Useful in the Practice of the Present Invention

Further, the desloratadine active ingredient may be administered in association with therapeutically effective amounts of one or more adjunct active ingredients selected from decongestants, aspirin, (acetysalicytic acid), acetaminophen, non-steroidal anti-inflammatory drugs (NSAIDs), cough suppressants, and expectorants. Said adjunct ingredients are dosed at levels known to those skilled in the art and as described in the *Physicians' Desk Reference*. Representative NSAIDs include, but are not limited to, naproxen, ibuprofen, ketoprofen, benoxaprofen, fluribiprofen, fenoprofen, fenbufen, indoprofen, pirprofen, carprofen, oxaprozin, pranoprofen, miroprofen, tioxaprofen, suprofen, alminoprofen, tiaprofenic acid, fluprofen, bucloxic acid, or pharmaceutically acceptable salts thereof. Combinations with decongestants are preferred.

Representative upper airway passage decongestants include, but are not limited to, phenylephrine, pseudoephedrine and phenylpropanolamine. Representative expectorants include, but are not limited to, guaiafenesin, terpin hydrate, guaiacolate potassium, potassium guaicolsulfonate. Representative cough suppressants include, but are not limited to, dextromethorphan, codeine and caramiphen.

The desloratadine/pharmaceutically acceptable carrier combination and the optional additional active ingredients may be administered as a combination or separately to treat or prevent breathing disorders associated with upper airway passage congestion especially nasal congestion which can lead to disordered sleep. The term "in association with " as used herein means that separate pharmaceutical compositions of desloratadine and the optional additional ingredients, such as an upper airway passage decongestant, may be administered concurrently or sequentially in a suitable order. Preferably, the desloratadine and optional additional ingredients are administered in a single dosage form.

REPRESENTATIVE DCL AND DCL COMBINATION THERAPIES

Example 1

A tablet containing 5 mg desloratadine and 240 mg pseudoephedrine is prepared according to methods known to those skilled in the art and administered to a patient in need of treatment.

Example 2

A tablet containing 5 mg desloratadine and 240 mg phenlpropanolamine is prepared and administered to a patient in need of treatment.

Example 3

A tablet containing 2.5 mg desloratadine and 120 mg pseudoephedrine is prepared according to methods known to those skilled in the art and administered to a patient in need of treatment.

Example 4

A tablet containing 2.5 mg desloratadine and 120 mg phenylpropanolamine is prepared according to methods known to those skilled in the art, and administered to a patient in need of treatment.

Example 5

A tablet containing 5 mg desloratadine is prepared according to methods known to those skilled in the art and administered to a patient in need of treatment.

A clinician skilled in the art of sleep disorder management understands that the desloratadine should be administered until the symptoms of upper airway passage disordered breathing leading to the particular sleep disorder are ameliorated.

The patient treated in accordance with the methods of the present inventor will enjoy relief of upper airway passage congestion resulting in uninterrupted sleep and will experience improved personal performance and workplace productivity without daytime somnolence associated with upper airway passage allergic inflammation and/or congestion associated with allergic rhinitis.

What is claimed is:

1. A method of treating and/or preventing sleep disorders in a human afflicted with upper airway passage allergic inflammation and/or congestion associated with seasonal allergic rhinitis comprising administering a therapeutically effective amount of desloratadine.

2. The method of claim 1 wherein the therapeutically effective amount of desloratadine is about 1 mg/day to about 20 mg/day.

3. The method of claim 1 wherein the therapeutically effective amount of desloratadine is about 5 mg/day to about 20 mg/day.

4. A method of treating and/or preventing sleep disorders in a human afflicted with upper airway passage allergic inflammation and/or congestion associated with perennial allergic rhinitis comprising administering a therapeutically effective amount of desloratadine.

5. The method of claim 4 wherein the therapeutically effective amount of desloratadine is about 1 mg/day to about 20 mg/day.

6. The method of claim 4 wherein the therapeutically effective amount of desloratadine is about 5 mg/day to about 20 mg/day.

7. A method of treating and/or preventing sleep disorders in a human afflicted with upper airway passage allergic inflammation and/or congestion associated with seasonal allergic rhinitis comprising administering a therapeutically effective amount of desloratadine in association with a therapeutically effective amount of an upper air way passage decongestant.

8. The method of claim 7, wherein the upper air way passage decongestant is pseudoephedrine or phenylpropanolamine or a pharmaceutically acceptable salt thereof.

9. The method of claim 7, wherein the decongestant is pseudoephedrine sulfate and the therapeutically effective amount of pseudoephedrine sulfate is 120 mg/day.

10. The method of claim 7 wherein the decongestant is pseudoephedrine sulfate and the therapeutically effective amount of pseudoephedrine sulfate is 240 mg/day.

11. The method of claim 7 wherein the therapeutically effective amount of desloratadine is about 1 mg/day to about 20 mg/day.

12. The method of claim 7 wherein the therapeutically effective amount of desloratadine is about 5 mg/day to about 20 mg/day.

13. A method of treating and/or preventing sleep disorders in a human afflicted with upper airway passage allergic inflammation and/or congestion associated with perennial allergic rhinitis comprising administering a therapeutically effective amount of desloratadine in association with a therapeutically effective amount of an upper air way passage decongestant.

14. The method of claim 13, wherein the upper air way passage decongestant is pseudoephedrine or phenylpropanolamine or a pharmaceutically acceptable salt thereof.

15. The method of claim 13, wherein the decongestant is pseudoephedrine sulfate and the therapeutically effective amount of pseudoephedrine sulfate is 120 mg/day.

16. The method of claim 13 wherein the therapeutically effective amount of pseudoephedrine sulfate is 240 mg/day.

17. The method of claim 13 wherein the therapeutically effective amount of desloratadine is about 1 mg/day to about 20 mg/day.

18. The method of claim 13 wherein the therapeutically effective amount of desloratadine is about 5 mg/day to about 20 mg/day.

19. A method of treating and/or preventing breathing disorders, associated with upper airway passage allergic nasal congestion in a human comprising administering a therapeutically effective amount of desloratadine in association with a therapeutically effective amount of an upper airway passage decongestant.

20. The method of claim 19, wherein the upper air way passage decongestant is pseudoephedrine or phenylpropanolamine or a pharmaceutically acceptable salt thereof.

21. The method of claim 19, wherein the deconggestant is pseudophedrine sulfate and the therapeutically effective amount of pseudoephedrine sulfate is 120 mg/day.

22. The method of claim 19 wherein the therapeutically effective amount of pseudoephedrine is 240 mg/day.

23. The method of claim 19 wherein the therapeutically effective amount of desloratadine is about 1 mg/day to about 20 mg/day.

* * * * *